(12) United States Patent
Bruchmann et al.

(10) Patent No.: US 7,022,874 B2
(45) Date of Patent: Apr. 4, 2006

(54) PREPARATION OF BIURET-CONTAINING POLYISOCYANATES

(75) Inventors: Bernd Bruchmann, Ludwigshafen (DE); Stefan Wolff, Limburgerhof (DE); Wolfgang Heider, Neustadt (DE); Joachim Jähme, Bobenheim-Roxheim (DE); Werner Langer, Ludwigshafen (DE); Hans Renz, Meckenheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 459 days.

(21) Appl. No.: 08/894,156

(22) PCT Filed: Feb. 1, 1996

(86) PCT No.: PCT/EP96/00419

§ 371 (c)(1),
(2), (4) Date: Aug. 15, 1997

(87) PCT Pub. No.: WO96/25444

PCT Pub. Date: Aug. 22, 1996

(65) Prior Publication Data

US 2003/0120108 A1     Jun. 26, 2003

(30) Foreign Application Priority Data

Feb. 15, 1995  (DE) ................. 195 05 035

(51) Int. Cl.
- *C07C 273/18* (2006.01)
- *C07C 273/00* (2006.01)
- *C07C 275/62* (2006.01)

(52) U.S. Cl. .................. 560/335; 560/336; 564/38
(58) Field of Classification Search ............... 560/335, 560/336; 564/38
See application file for complete search history.

(56) References Cited

U.S. PATENT DOCUMENTS

| | | | | |
|---|---|---|---|---|
| 3,124,605 A | * | 3/1964 | Wagner | 560/335 |
| 3,358,010 A | * | 12/1967 | Britain | 560/335 |
| 3,367,956 A | * | 2/1968 | Hennig et al. | 560/335 |
| 3,903,127 A | * | 9/1975 | Wagner et al. | 560/335 |
| 3,976,622 A | | 8/1976 | Wagner et al. | 528/49 |
| 4,028,392 A | | 6/1977 | Ogawa et al. | 560/357 |
| 4,051,165 A | * | 9/1977 | Wagner et al. | 560/335 |
| 4,062,833 A | * | 12/1977 | Van Eyck et al. | 528/44 |
| 4,127,599 A | * | 11/1978 | Mohring et al. | 521/162 |
| 4,147,714 A | * | 4/1979 | Hetzel et al. | 560/335 |
| 4,152,350 A | * | 5/1979 | Mohring et al. | 521/160 |
| 4,181,782 A | * | 1/1980 | Mohring et al. | 521/162 |
| 4,192,936 A | * | 3/1980 | Mohring et al. | 528/59 |

FOREIGN PATENT DOCUMENTS

| | | |
|---|---|---|
| DE | 1 101 394 | 4/1958 |
| DE | 12 27 004 | 10/1966 |
| DE | 1 543 178 | 7/1969 |
| DE | 19 31 055 | 12/1970 |
| FR | 1 375 463 | 9/1964 |
| FR | 1 475 617 | 2/1967 |

OTHER PUBLICATIONS

Journal Fur Praktische Chemie Chemiker-Zeitung, cf. H.J. LAAS, et al., vol. 336 (1994) 185-200.

* cited by examiner

*Primary Examiner*—Rabon Sergent
(74) *Attorney, Agent, or Firm*—Oblon, Spivak, McClelland, Maier & Neustadt, P.C.

(57) ABSTRACT

A process for the preparation of polyisocyanates which contain one or more biuret groups, by reacting
a) an aliphatic or cycloaliphatic isocyanate containing two or more isocyanate groups (isocyanate a) with
b) a tertiary alcohol or a mixture of water and a tertiary alcohol (biuretizing agent b)
at from 100 to 250° C., which comprises carrying out the reaction in the presence
c) of a stabilizer (c) which constitutes a catalytic amount of urea, ammonia, biuret, a urea derivative of the formula I

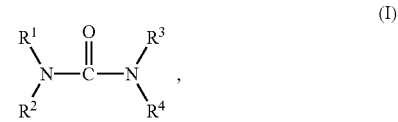

in which $R^1$, $R^2$, $R^3$ and $R^4$ are hydrogen, $C_1$ to $C_{10}$ alkyl or $C_5$ to $C_{10}$ aryl, or
a carboxamide of the formula II

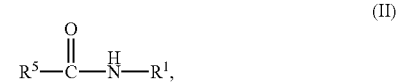

in which $R^5$ is $C_1$ to $C_{12}$ alkyl which is unsubstituted or in which 1, 2 or 3 hydrogen atoms are replaced by a radical

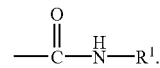

16 Claims, No Drawings

US 7,022,874 B2

PREPARATION OF BIURET-CONTAINING POLYISOCYANATES

BACKGROUND OF THE INVENTION

1. Field of the Invention

The present invention relates to a process for the preparation of polyisocyanates which contain one or more biuret groups, by reacting
a) an aliphatic or cycloaliphatic polyisocyanate (isocyanate a) with
b) a tertiary alcohol or a mixture of water and a tertiary alcohol (biuretizing agent b)

at from 100 to 250° C.

2. Description of the Background

In the text below, the adjective "biuret-containing" indicates that the compounds it describes have a content of biuret groups.

The preparation of biuret-containing polyisocyanates is a reaction which has been described at some length (cf. H. J. Laas et al., J. prakt. Chem. 336 (1994) 185–200).

Numerous patents disclose, for example, the reaction of water with an excess of polyvalent isocyanates to give, first of all, urea groups, which undergo further reaction with the isocyanates to form biuret groups (cf. DE-A 1 101 394). The difficulty of preparing homogenous mixtures of water and the isocyanate means that in the course of this reaction, in practice, local excesses of water always result in the formation of greater or lesser proportions of insoluble polymeric urea-containing compounds which are deposited in the reaction vessel or in the off-gas space.

U.S. Pat. No. 4,028,392 describes a process in which this problem is avoided by employing water in the form of an aqueous solution with a solvent which is inert to isocyanates. The disadvantage here is the need to separate the solvent from the product again by distillation.

SUMMARY OF THE INVENTION

These problems can be overcome using the process known from DE-A 1 543 178, in which a monohydric tertiary alcohol such as tert-butanol is used instead of water. The alcohol reacts at 70° C. or more with an excess of isocyanate to form biuret-containing polyisocyanates and, as by-products, an olefin—isobutene for example—and $CO_2$, which can be removed from the reaction mixture with ease.

It is probable that the alcohol and the isocyanate react initially to form a urethane which decomposes into an amine, $CO_2$ and an olefin, and that the amine reacts with further isocyanate to give urea derivatives, and then to give biuret-containing polyisocyanates.

This reaction is preferably carried out in the presence of catalysts, with those recommended for this being acids such as strong inoganic Lewis and Brönstedt acids (cf. DE-A 1 543 178) and salts of nitrogen-containing bases and inorganic and/or organic acids (cf. DE-A 1 931 055).

Biuret-containing polyisocyanates are employed in particular in the paint industry as curing agents in coating systems whose binders generally comprise polymers having isocyanate-reactive groups.

So that the coating systems cure within a short period after application to a substrate to give coatings of good mechanical properties and high resistance to chemicals, it is necessary for the biuret-containing polyisocyanates to have a high content of NCO groups and a high level of reactivity with respect to the reactive groups in the binders.

In addition, the proportion of volatile isocyanates should be small even after prolonged storage, so as to enable safe processing of the biuret-containing polyisocyanates without the need for special safety precautions. So that these can be used to produce coating systems which exhibit good flow properties and a low solvent content, the paint industry demands products which at the same time are of low viscosity. Furthermore, the inherent color of the products should be minimal.

The biuret-containing polyisocyanates prepared by the known processes from tertiary alcohols and isocyanates, however, leave much to be desired, since they are too dark in color for many applications and, in particular after prolonged storage, still include considerable quantities of readily volatile monomeric isocyanates.

It is the object of the invention to provide an economic process by whose use it is possible to prepare biuret-containing polyisocyanates which are pale in color and whose content of volatile isocyanates, in particular after prolonged storage, is low.

We have found that this object is achieved by a process for the preparation of polyisocyanates which contain one or more biuret groups, by reacting
a) an aliphatic or cycloaliphatic isocyanate containing two or more isocyanate groups (isocyanate a) with
b) a tertiary alcohol or a mixture of water and a tertiary alcohol (biuretizing agent b)

at from 100 to 250° C., which comprises carrying out the reaction in the presence
c) of a stabilizer (c) which constitutes a catalytic amount of urea, ammonia, biuret, a urea derivative of the formula I

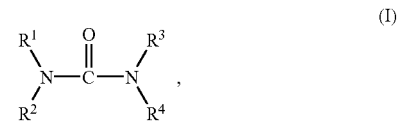

in which $R^1$, $R^2$, $R^3$ and $R^4$ are hydrogen, $C_1$ to $C_{10}$ alkyl or $C_5$ to $C_{10}$ aryl, or
a carboxamide of the formula II

in which $R^5$ is $C_1$ to $C_{12}$ alkyl which is unsubstituted or in which 1, 2 or 3 hydrogen atoms are replaced by a radical

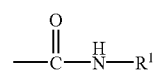

DETAILED DESCRIPTION OF THE INVENTION

Among the starting materials for the process of the invention, suitable isocyanates (a) are polyfunctional isocyanates, especially aliphatic and cycloaliphatic di- and triisocyanates containing 4 to 30 carbon atoms. Particular examples are diisocyanates $X(NCO)_2$ in which X is an aliphatic hydrocarbon radical of 4 to 12 carbon atoms or a cycloaliphatic hydrocarbon radical of 6 to 15 carbon atoms. Of particular significance in this respect are the commercially available starting compounds which are prepared industrially by the phosgenization of diamines by the process as described, for example, in DE-C 20 05 309 and DE-A 2 404 773 and by the phosgene-free process (biurethane cleavage) described in EP-B-0 126 299 (U.S. Pat. No. 4,596,678), EP-B-0 126 300 (U.S. Pat. No. 4,596,679), EP-A-0 355 443 (U.S. Pat. No. 5,087,739) and EP-A-0 568 782.

These are, in particular, 1,6-diisocyanatohexane (HDI), 1-isocyanato-3-isocyanatomethyl-3,5,5-trimethylcyclohexane (IPDI) and bis(4-isocyanatocyclohexyl)methane.

Starting compounds which are of less importance in practice but of equal suitability in principle are isocyanates comprising 3 or more isocyanate groups, for example those which in addition include allophanate or isocyanurate groups. Examples of these are the corresponding derivatives of HDI which are prepared by trimerization of HDI (cf. Kunststoff-Handbuch, volume 7, pp. 94 to 96, 3rd edition, 1993, Carl Hanser Verlag).

Particularly suitable biuretizing agents (b) are the tertiary alcohols specified in DE-A 1 543 178, ie. especially monohydric alcohols of 4 to 20 carbon atoms, examples being 2-methyl-2-butanol, 2-methyl-2-pentanol, 3-methyl-3-pentanol, 3-ethyl-3-pentanol, 3-ethyl-3-nonanol, 3-methyl-1-butyn-3-ol, 3-methyl-1-pentyn-3-ol, 3,5-dimethyl-1-hexyn-3-ol, 1-methylcyclopentanol, 1-methylcyclohexanol, 1-ethylcyclohexanol, 1,1-diphenylethanol, 1,1,2-triphenylethanol and, in particular, tert-butyl alcohol. Mixtures of these alcohols are of course also suitable.

In addition to the tertiary alcohols, water in the form of an aqueous solution with the tertiary alcohols can also be used to biuretize the isocyanates (a). In this context, particularly suitable solutions of tertiary alcohol and water are those containing up to 80 mol %, preferably up to 40 mol %, of water, based on the sum of the components of the mixture, since at these mixing ratios water is incorporated homogeneously and no oligomeric or polymeric urea derivatives, which precipitate from the reaction mixture, are formed in the course of the reaction with the isocyanates (a).

In accordance with the invention, the isocyanate (a) is reacted with the biuretizing agent (b) in the presence of catalytic amounts of a stabilizer (c).

Suitable stabilizers (c) are urea, ammonia, biuret, a urea derivative of the formula I

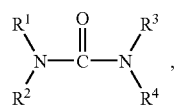

in which $R^1$, $R^2$, $R^3$ and $R^4$ are hydrogen, $C_1$ to $C_{10}$ alkyl, preferably methyl or ethyl, or $C_5$ to $C_{10}$ aryl, preferably phenyl or benzyl, or a carboxamide of the formula II

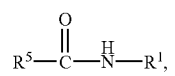

in which $R^5$ is a $C_1$ to $C_{12}$ alkyl, preferably $C_1$ to $C_6$ alkyl, which is unsubstituted or in which 1, 2 or 3 hydrogen atoms are replaced by a radical

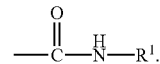

Examples of suitable urea derivatives are N-methylurea, N,N-dimethylurea, N,N'-dimethylurea, N-ethylurea, N,N-diethylurea, N,N'-diethylurea, ethyleneurea and N-phenylurea.

Suitable carboxamides of the formula II are formamide, N-methylformamide, acetamide, malonamide and succinamide.

The stabilizers (c) are preferably employed in quantities of from 0.01 to 2.0 mol %, and with particular preference in quantities of from 0.05 to 1 mol %, based on the isocyanate groups in (a).

Using the process of the invention, the biuret-containing polyisocyanate can be prepared either continuously or batchwise.

A suitable apparatus for continuous preparation is, for example, a reactor cascade comprising a plurality of individual reactors through which there is a continuous flow.

Batchwise preparation can be carried out, for example, in a stirred reactor.

Normally, the isocyanate (a) is taken as initial charge and the biuretizing agent (b), in which the stabilizer (c) is advantageously already dissolved, is metered in.

The reaction is preferably carried out in bulk, although to reduce the viscosity it is also possible to use a solvent which is inert to isocyanate groups. Suitable solvents are those mentioned in DE-A 1 543 178, dioxane, tetrahydrofuran, triethylene glycol diacetate, toluene, benzene, chlorobenzene, o-dichlorobenzene, butyl acetate, ethylene glycol monoethyl ether acetate and methylene chloride.

In general the reaction is carried out under atmospheric pressure, although higher pressures of 1 to 10 bar are advisable, for example, when using solvents or isocyanates (a) which boil below the preferred reaction temperatures.

At the preferred temperatures, the reaction times are in general from 2 to 5 h. The reaction time is advantageously chosen such that the theoretical NCO value is reached at the end. The theoretical NCO value is that NCO value possessed by the reaction mixture if the entire quantity of biuretizing agent employed has formed the quantity of biuret groups which are to be expected from theory.

As is known, the result of reacting an isocyanate group with a molecule of water or tertiary alcohol is an amino group which reacts with two further isocyanate groups to form a biuret group. Since the starting compounds employed include polyfunctional isocyanates, the growth of the biuret-containing polyisocyanates therefore takes place in accordance with the kinetics of crosslinking reactions (cf. B. Vollmert, Grundriβ der Makromolekularen Chemie, volume II, pp. 247 to 260, Vollmert-Verlag, Karlsruhe, 1988), with each biuret group forming a branching point. In order to avoid the formation of relatively large branched-chain associations with two or more branching points, or even the occurrence of gelling, it is generally advisable to employ from 0.5 to 20 mol %, preferably from 2 to 10 mol %, of biuretizing agent, based on the isocyanate groups in (a).

Under these conditions, the isocyanates (a) react with the biuretizing agents predominantly to form mixtures of biuret-containing polyisocyanates whose principal component comprises those biuret-containing polyisocyanates which are composed of three units derived from the isocyanate (a), containing only one biuret group.

Otherwise, it is possible by simple prior experimentation or calculation to determine the stoichiometric ratios at which mixtures of biuret-containing polyisocyanates are formed which have the desired average degree of polymerization.

In general, in order to obtain products which do not release hazardous quantities of isocyanates during processing, it is necessary to separate off the majority of the unreacted isocyanates (a) from the biuret-containing polyisocyanates formed. The usual desire is for products whose content of monomeric isocyanates (a) is less than 1% by weight, preferably less than 0.5% by weight, based on said biuret-containing polyisocyanates. The separation of the isocyanates (a) is advantageously carried out under reduced pressure at between 50° C. and the chosen reaction temperature, for example by distilling off these isocyanates.

In the paint industry, the desire is in particular for biuret-containing polyisocyanates wich are substantially free of solvents and from the isocyanates (a) used as starting materials, and which have a viscosity of from 2000 to 15,000 mPa·s, preferably from 2500 to 10,000 mPa·s (measured at a temperature of 23° C. and a shear gradient of 100 s$^{-1}$).

Products with these viscosities are in general obtained when the stoichiometry of the starting products, the isocyanates (a) and the biuretizing agents (b), is chosen in accordance with the recommendation.

The products obtained by this process are distinguished in particular in that they couple comparatively low viscosity and a low content of volatile isocyanates of low molecular weight, like the isocyanates (a) used as starting materials, with a high NCO content and a high reactivity with respect to the binders employed in coatings, said binders containing isocyanate-reactive groups and being, for example, hydroxyl-containing polyacrylates. Particular advantages are that the content of volatile isocyanates does not rise even on prolonged storage of the products, and that the products are substantially colorless.

The products obtained by the process of the invention are particularly suitable as curing agents in the paint industry. The processing of these curing agents to give coating formulations, and the coatings produced therefrom, are items of general knowledge.

EXAMPLES

General Preparation Procedure for the Biuret-containing Polyisocyanates (a)

504 g (3 mol) of 1,6-hexamethylene diisocyanate (HDI) are charged under nitrogen blanketing to a 1 stirred reactor, and are heated to the reaction temperature indicated in the tables below. Then 14 mol %, based on the HDI, of biuretizing agent (b) and, dissolved therein, 0.2 mol %, based on the HDI, of the stabilizer (c) or of the acidic catalyst are added over the course of 2 min and the reaction mixture is stirred for 3 h. The reaction mixture is then distilled on a thin-film evaporator at 165° C. and 2.5 mbar.

Departing from the above indications, the quantity of urea employed was 0.4 mol % in Example 11, 0.6 mol % in Example 12, and 1.0 mol % in Example 13, based in each case on the quantity of HDI.

TABLE 1

| Ex. | Biuretizing agent (b) | Stabilizer (c) | Temp. [° C.] | NCO content [% by wt.] | Viscosity [mPa · s] | C N [Hazen] | Monomer content 0 d [% by wt.] | 21 d [% by wt.] |
|---|---|---|---|---|---|---|---|---|
| 1 | tert-Butanol (tBuOH) | UR | 180 | 22.0 | 4350 | 5 | 0.15 | 0.25 |
| 2 | tBuOH | Eth UR | 180 | 22.7 | 2290 | 10 | 0.20 | 0.41 |
| 3 | tBuOH:water 19:1 | UR | 170 | 22.4 | 3340 | 7 | 0.08 | 0.22 |
| 4 | tBuOH:water 19:1 | UR | 190 | 22.0 | 6030 | 10 | 0.10 | 0.21 |
| 5 | tBuOH:water 19:1 | Eth UR | 180 | 22.7 | 2200 | 12 | 0.15 | 0.45 |
| 6 | tBuOH:water 19:1 | DM UR | 180 | 22.7 | 2280 | 15 | 0.13 | 0.43 |
| 7 | tBuOH:water 4.6:1 | UR | 180 | 22.2 | 5550 | 5 | 0.11 | 0.23 |
| 8 | tBuOH:water 1.8:1 | UR | 180 | 22.0 | 6480 | 2 | 0.13 | 0.28 |
| 9 | tBuOH:water 1:1 | UR | 180 | 22.2 | 5450 | 4 | 0.14 | 0.31 |
| 10 | tBuOH:water 0.27:1 | UR | 180 | 21.4 | 12,600 | 10 | 0.14 | 0.28 |
| 11 | tBuOH:water 1:1 | UR | 180 | 22.0 | 6120 | 12 | 0.12 | 0.27 |
| 12 | tBuOH:water 1:1 | UR | 180 | 21.3 | 11,560 | 18 | 0.12 | 0.29 |
| 13 | tBuOH:water 1:1 | UR | 180 | 20.8 | 18,200 | 22 | 0.13 | 0.25 |
| 14 | tBuOH:water 19:1 | Biuret | 180 | 22.0 | 3860 | 15 | 0.14 | 0.27 |
| 15 | tBuOH:water 19:1 | Acetamide | 180 | 22.6 | 3020 |  | 0.17 | 0.31 |
| 16 | tBuOH:water 19:1 | Samid | 180 | 22.5 | 3000 |  | 0.14 | 0.34 |
| 17 | tBuOH:water 19:1 | Ammonia | 180 | 22.0 | 2340 | 28 | 0.21 | 0.50 |

TABLE 2

| Comp. Ex. | Biuretizing agent (b) | Acidic catalysts | Temp. [° C.] | NCO content [% by wt.] | Viscosity [mPa · s] | C N [Hazen] | Monomer content 0 d [% by wt.] | 21 d [% by wt.] |
|---|---|---|---|---|---|---|---|---|
| 1 | tert-Butanol (tBuOH) | BF$_3$ | 150 | 22.9 | 2550 | 206 | 0.09 | 0.69 |
| 2 | tBuOH | PTSS | 150 | 21.7 | 5400 | 350 | 0.05 | 0.48 |
| 3 | tBuOH | DEHP | 180 | 22.0 | 4840 | 42 | 0.07 | 0.42 |

TABLE 2-continued

| Comp. Ex. | Biuretizing agent (b) | Acidic catalysts | Temp. [°C.] | NCO content [% by wt.] | Viscosity [mPa·s] | C N [Hazen] | Monomer content | |
|---|---|---|---|---|---|---|---|---|
| | | | | | | | 0 d [% by wt.] | 21 d [% by wt.] |
| 4 | tBuOH | EHA | 180 | 22.0 | 4660 | 38 | 0.09 | 0.42 |
| 5 | tBuOH | HAc | 180 | 22.1 | 4330 | 55 | 0.08 | 0.40 |
| 6 | tBuOH | — | 180 | 22.9 | 2130 | 44 | 0.09 | 0.53 |
| 7 | tBuOH:water 19:1 | PTSS | 180 | 22.0 | 5550 | 371 | 0.11 | 0.91 |
| 8 | tBuOH:water 19:1 | PTSS | 150 | 21.8 | 5360 | 256 | 0.03 | 0.49 |
| 9 | tBuOH:water 19:1 | DEHP | 180 | 22.4 | 3800 | 32 | 0.10 | 0.53 |
| 10 | tBuOH:water 19:1 | EHA | 180 | 22.4 | 3650 | 10 | 0.15 | 0.63 |
| 11 | tBuOH:water 19:1 | ClAc | 180 | 22.3 | 3970 | 56 | 0.14 | 0.53 |
| 12 | tBuOH:water 19:1 | — | 180 | 22.7 | 2090 | 32 | 0.12 | 0.61 |

Notes on Tables 1 and 2

Compounds Employed

The biuretizing agents employed were tert-butanol (tBuOH) and mixtures thereof with water. The figures given thereafter indicate the molar ratio of the components in the mixture UR=urea
EthUR=ethyleneurea
DM UR=N,N'-dimethylurea
$BF_3$=boron trifluoride as the dihydrate
PTSA=p-toluenesulfonic acid
DEHP=di(2-ethylhexyl) phosphate
EHA=2-ethylhexanoic acid
HAc=acetic acid
Samid=succinamide
ClAc=chloroacetic acid
Ammonia=ammonia in the form of a 25% strength by weight aqueous solution NCO Content:

The NCO content is given in % by weight and was measured in accordance with DIN 53 185.

Viscosity:

The viscosity data relate to measurements made at 23° C. with a shear gradient of 100 s$^{-1}$.

Color Number (CN):

The color number was determined in accordance with DIN ISO 6271 and is indicated in Hazen scale units.

Monomer Content:

The monomer content indicates the quantity of monomeric isocyanate in % by weight present in the respective biuret-containing polyisocyanate directly after preparation (0 d) or after storage for 21 days at 50° C. (21 d). It was measured in accordance with DIN 55 956.

We claim:

1. A process for the preparation of a polyisocyanate which contains one or more biuret groups by reacting
   a) an aliphatic or cycloaliphatic isocyanate containing two or more isocyanate groups (isocyanate (a)) with
   b) 0.5 to 20 mol % based on the isocyanate groups in (a) of a tertiary alcohol or a mixture of water and a tertiary alcohol (biuretizing agent (b)) at from 100 to 250° C., which comprises carrying out the reaction in the presence
   c) from 0.01 to 2.0 mol % based on the isocyanate groups in (a) of a stabilizer (c) selected from the group consisting of urea, ammonia, biuret, ethylene urea, a urea derivative of the formula I

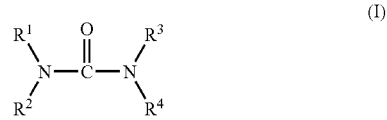

in which $R^1$, $R^2$, $R^3$ and $R^4$ are hydrogen, $C_1$ to $C_{10}$ alkyl or $C_6$ to $C_{10}$ aryl, or a carboxamide of the formula II

in which $R^5$ is $C_1$ to $C_{12}$ alkyl which is unsubstituted or in which 1, 2 or 3 hydrogen atoms are replaced by a radical

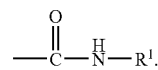

2. A process as claimed in claim 1, wherein the isocyanate (a) is a $C_4$ to $C_{30}$ diisocyanate or triisocyanate.

3. A process as claimed in claim 1, wherein the isocyanate (a) is hexamethylene-1,6-diisocyanate.

4. A process as claimed in claim 1, wherein the biuretizing agent (b) is a tertiary alcohol or a mixture of a tertiary alcohol and up to 80 mol % of water based on the sum of the components of the mixture.

5. A process as claimed in claim 1, wherein the tertiary alcohol is tert-butanol.

6. A process as claimed in claim 1, wherein the reaction is carried out at from 140 to 220° C.

7. A process as claimed in claim 1, wherein the polyisocyanate containing biuret groups is prepared and then unreacted isocyanate (a) is removed from it down to a content of less than 0.5% by weight, based on the polyisocyanate which contains biuret groups.

8. A process as claimed in claim 1, wherein the stabilizer (c) is urea.

9. A process as claimed in claim 1, wherein the stabilizer (c) is ammonia.

10. A process as claimed in claim 1, wherein the stabilizer (c) is biuret.

11. A process as claimed in claim 1, wherein the stabilizer (c) is ethyleneurea.

12. A process as claimed in claim 1, wherein the stabilizer (c) is a urea derivative of the formula I.

13. A process as claimed in claim 12, wherein the stabilizer (c) is N,N'-dimethylurea.

14. A process as claimed in claim 1, wherein the stabilizer (c) is a carboxamide of the formula II.

15. A process as claimed in claim 14, wherein the stabilizer (c) is acetamide.

16. A process as claimed in claim 14, wherein the stabilizer (c) is succinamide.

* * * * *